(12) United States Patent
Ryzhikov

(10) Patent No.: US 9,671,337 B2
(45) Date of Patent: Jun. 6, 2017

(54) HIGH NUMERICAL APERTURE OBJECTIVE LENS SYSTEM

(71) Applicant: ASML Holding N.V., Veldhoven (NL)

(72) Inventor: Lev Ryzhikov, Norwalk, CT (US)

(73) Assignee: ASML Holding N.V., Veldhoven (NL)

( * ) Notice: Subject to any disclaimer, the term of this patent is extended or adjusted under 35 U.S.C. 154(b) by 0 days.

(21) Appl. No.: 15/243,269

(22) Filed: Aug. 22, 2016

(65) Prior Publication Data

US 2016/0356710 A1 Dec. 8, 2016

Related U.S. Application Data

(62) Division of application No. 14/819,335, filed on Aug. 5, 2015, now Pat. No. 9,513,559.

(Continued)

(51) Int. Cl.
| | |
|---|---|
| *G03B 27/54* | (2006.01) |
| *G01N 21/47* | (2006.01) |
| *G03F 7/20* | (2006.01) |
| *G02B 13/14* | (2006.01) |
| *G01N 21/95* | (2006.01) |

(Continued)

(52) U.S. Cl.
CPC ....... *G01N 21/474* (2013.01); *G01N 21/8806* (2013.01); *G01N 21/9501* (2013.01); *G02B 9/64* (2013.01); *G02B 13/143* (2013.01); *G02B 13/16* (2013.01); *G02B 13/18* (2013.01); *G02B 21/02* (2013.01); *G02B 27/0025* (2013.01); *G03F 7/70* (2013.01); *G03F 7/70058* (2013.01); *G01N 2201/0638* (2013.01)

(58) Field of Classification Search
CPC .......................... G03F 7/70058; G03F 7/70075

USPC .................................. 355/52, 53, 55, 67–71
See application file for complete search history.

(56) References Cited

U.S. PATENT DOCUMENTS

| | | |
|---|---|---|
| 5,444,573 A | 8/1995 | Saito |
| 5,867,326 A | 2/1999 | Yamamoto |

(Continued)

FOREIGN PATENT DOCUMENTS

| | | |
|---|---|---|
| EP | 1 628 164 A2 | 2/2006 |
| EP | 2 579 100 Z2 | 4/2013 |

(Continued)

OTHER PUBLICATIONS

English-Language Machine Translation of Description and Claims for Russian Patent Publication No. SU 903786 A, published Feb. 7, 1982; 3 pages.

(Continued)

*Primary Examiner* — Hung Henry Nguyen
(74) *Attorney, Agent, or Firm* — Sterne, Kessler, Goldstein & Fox P.L.L.C.

(57) ABSTRACT

An objective lens system having a high numerical aperture, a large working distance, and low optical aberrations over a wide spectral band of wavelengths is disclosed. The objective lens system includes a first lens group, a second lens group, and a third lens group. The first lens group includes first and second positive meniscus lenses that are positioned at a distance from each other along an optical axis of the objective lens system. The distance may be dependent on a focal length of the objective lens system. The second lens group includes first and second meniscus lenses and a bi-convex lens. The third lens group includes a bi-concave lens and a doublet lens.

6 Claims, 5 Drawing Sheets

Related U.S. Application Data

(60) Provisional application No. 62/056,701, filed on Sep. 29, 2014.

(51) Int. Cl.
*G01N 21/88* (2006.01)
*G02B 21/02* (2006.01)
*G02B 9/64* (2006.01)
*G02B 13/16* (2006.01)
*G02B 13/18* (2006.01)
*G02B 27/00* (2006.01)

(56) References Cited

U.S. PATENT DOCUMENTS

| | | | |
|---|---|---|---|
| 5,940,220 | A | 8/1999 | Suenaga et al. |
| 6,016,226 | A | 1/2000 | Arisawa |
| 6,069,744 | A | 5/2000 | Kusaka et al. |
| 6,501,603 | B2 | 12/2002 | Kasahara |
| 7,050,223 | B1 | 5/2006 | Hoppen |
| 7,440,154 | B2 | 10/2008 | Zeng et al. |
| 7,633,689 | B2 | 12/2009 | Shmarev et al. |
| 2003/0053218 | A1 | 3/2003 | Fujimoto et al. |
| 2003/0165021 | A1 | 9/2003 | Kawasaki |
| 2005/0207021 | A1 | 9/2005 | Yamaguchi |
| 2008/0198475 | A1 | 8/2008 | Arimoto et al. |
| 2011/0063735 | A1 | 3/2011 | Yamaguchi |
| 2013/0003187 | A1 | 1/2013 | Wartmann |
| 2013/0083306 | A1* | 4/2013 | Smirnov .......... G03F 7/70633 355/67 |
| 2013/0148202 | A1 | 6/2013 | Yoshida |
| 2016/0091797 | A1 | 3/2016 | Ryzhikov |

FOREIGN PATENT DOCUMENTS

| | | |
|---|---|---|
| JP | S61/240218 A | 10/1986 |
| JP | 2013/140393 A | 7/2013 |
| SU | 903786 | 2/1982 |

OTHER PUBLICATIONS

English-Language Abstract for Japanese Patent Publication No. JP S61/240218 A, published Oct. 25, 1986; 2 pages.
English-Language Abstract for Japanese Patent Publication No. JP 2013/140393 A, published Jul. 18, 2013; 2 pages.
International Search Report and Written Opinion directed to related International Application No. PCT/EP2015/067352, mailed Jan. 25, 2016; 16 pages.

* cited by examiner

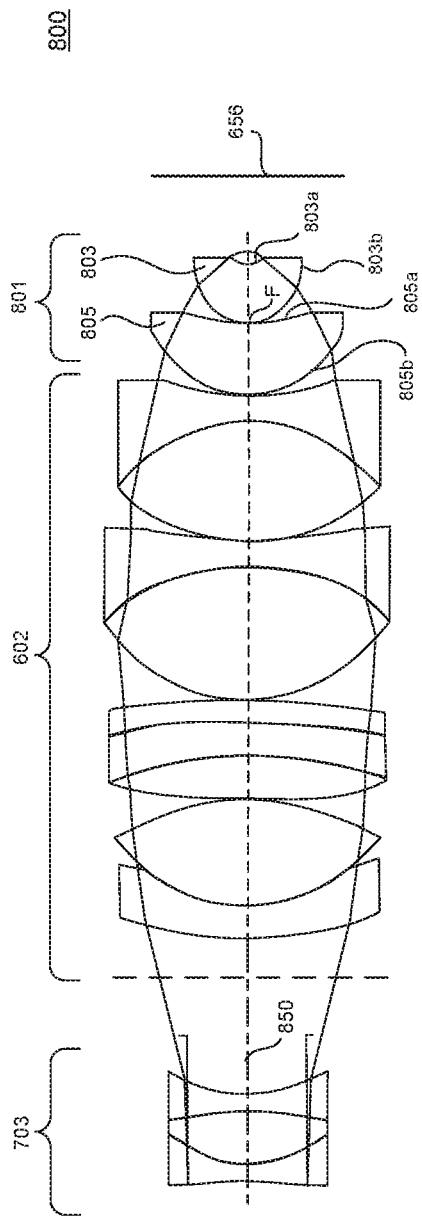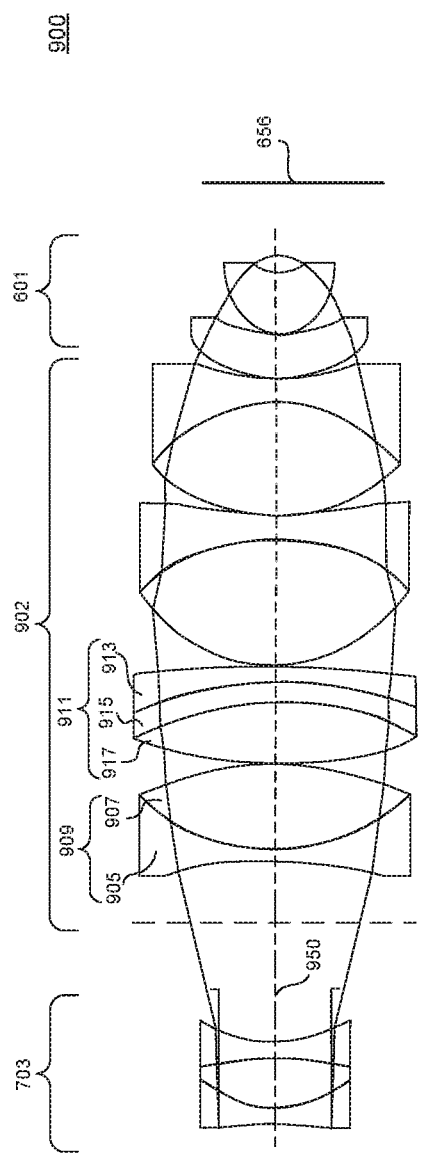
FIG. 8
FIG. 9

HIGH NUMERICAL APERTURE OBJECTIVE LENS SYSTEM

This application incorporates by reference in their entireties U.S. patent application Ser. No. 14/819,335, and U.S. provisional application 62/056,701.

FIELD

The present disclosure relates to various configurations of an objective lens system that may be used in, for example, an inspection system of a lithographic apparatus.

BACKGROUND

A lithographic apparatus is a machine that applies a desired pattern onto a target portion of a substrate. Lithographic apparatus can be used, for example, in the manufacture of integrated circuits (ICs). In that circumstance, a patterning device, which is alternatively referred to as a mask or a reticle, may be used to generate a circuit pattern corresponding to an individual layer of the IC, and this pattern can be imaged onto a target portion (e.g., comprising part of, one or several dies) on a substrate (e.g., a silicon wafer) that has a layer of radiation-sensitive material (resist). In general, a single substrate will contain a network of adjacent target portions that are successively exposed. Known lithographic apparatus include so-called steppers, in which each target portion is irradiated by exposing an entire pattern onto the target portion in one go, and so-called scanners, in which each target portion is irradiated by scanning the pattern through the beam in a given direction (the "scanning"-direction) while synchronously scanning the substrate parallel or anti parallel to this direction. It is also possible to transfer the pattern from the patterning device to the substrate by imprinting the pattern onto the substrate.

In lithographic processes, the patterned substrate and/or the reticle may be inspected for, e.g., process control and verification. There are various techniques for performing such inspection, including the use of scanning electron microscopes, and various specialized inspection systems, which may be used to detect defects on the reticle and/or measure, for example, critical dimension (CD) of the patterns on the substrate, overlay error between successive layers formed on the substrate. One type of specialized inspection system is a scatterometer in which a radiation beam is directed onto a target of the pattern on the surface of the substrate and one or more properties of the scattered or reflected radiation beam, for example, intensity at a single angle of reflection as a function of wavelength, intensity at one or more wavelengths as a function of reflected angle, or polarization as a function of reflected angle are measured to obtain a spectrum from which a property of interest of the target may be determined. Determination of the property of interest may be performed by various techniques, such as but not limited to reconstruction of the target structure by iterative approaches (e.g., rigorous coupled wave analysis or finite element methods), library searches, and/or principal component analysis. Two main types of scatterometer are known. Spectroscopic scatterometer that directs a broadband radiation beam onto the substrate and measure the spectrum (intensity as a function of wavelength) of the radiation beam scattered into a particular narrow angular range. Angularly resolved scatterometer that use a monochromatic radiation beam and measure the intensity of the scattered radiation beam as a function of angle.

Objective lens systems are used in these scatterometers for directing and/or focusing the radiation beam onto the object of inspection (e.g., the reticle, the target of the pattern on the surface of the substrate) and for collecting and/or imaging the scattered or reflected light from the object of inspection. The amount of information obtained from the collected light and/or from the images of the object may depend on the numerical aperture (NA) of the objective lens system and the wavelengths of the radiation beam used in the scatterometers. The higher the NA of the objective lens system and the wider the spectral band of wavelengths used in the scatterometers, the greater is the amount of information that can be obtained from the illuminated object of inspection. However, the highest NA and the maximum spectral bandwidth that can be used in an inspection system are limited by the design and configuration of one or more lenses in the objective lens system.

There are three types of high NA objective lens systems currently used for scatterometry applications: refractive, reflective, and catadioptric. Certain disadvantages are associated with the use of these current objective lens systems. One of the disadvantages of current high NA refractive objective lens system is that the working distance is relatively small. For example, the working distance is generally less than 0.35 mm for high NA (e.g., 0.9-0.95). Another one of the disadvantages is that the spectral band of wavelengths over which the current high NA refractive objective lens system can operate without compromising optical performance is limited to wavelengths ranging from about 450-700 nm. Use of current refractive objective lens systems outside this spectral band of wavelengths (e.g., below 450 nm wavelength, above 700 nm wavelength, between 410-450 nm wavelengths, between 700-900 nm wavelengths, at deep ultra violet (DUV) wavelengths, at infrared (IR) wavelengths) results in a loss of resolution due to chromatic aberrations (axial color aberrations). Loss of resolution can lead to reduced accuracy of the scatterometer measurements.

One of the disadvantages of current catadioptric and/or reflective objective lens systems is that they have a large Petzval sum that is far from zero (i.e., they do not have a flat field curvature) and as a result induce field curvature aberration. Pupil aberration is another one of the disadvantages of the current catadioptric and/or reflective objective lens systems due to their large field curvature and pupil size. Further, the current catadioptric and/or reflective objective lens systems suffer from obscuration that reduces the amount of collected light, and hence, the amount of information that can be collected from the object of inspection.

SUMMARY

Accordingly, there is a need for an improved objective lens system that can be configured to have a high NA without the above mentioned disadvantages.

According to an embodiment, an objective lens system includes a first lens group comprising first and second positive meniscus lenses that may be positioned at a distance from each other along an optical axis of the objective lens system. The distance may be dependent on a focal length of the objective lens system. The objective lens system further includes a second lens group comprising a triplet lens. The triplet lens may comprise a first meniscus lens having a first surface and a second surface, a second meniscus lens having a third surface and a fourth surface, and a bi-convex lens having a fifth surface and a sixth surface. The third surface may be in substantial contact with the second surface and the fifth surface may be in substantial contact with the fourth surface. The objective lens system may further include a third lens group comprising a bi-concave lens and a doublet lens.

In another embodiment, an inspection system may be configured to measure a property of a substrate. The inspection system includes a radiation source that may be configured to produce a radiation beam, an optical system that may be configured to focus the radiation beam on to a surface of the substrate, and a detector that may be configured to detect the radiation beam reflected from the surface of the substrate. The optical system may comprise a first lens group comprising first and second positive meniscus lenses that may be positioned at a distance from each other along an optical axis of the objective lens system. The distance may be dependent on a focal length of the objective lens system. The optical system may further comprise a second lens group comprising a third positive meniscus lens, a negative meniscus lens cemented to the third positive meniscus lens, and a bi-convex lens cemented to the negative meniscus lens. The optical system may also comprise a third lens group comprising a bi-concave lens and a doublet lens.

Yet in another embodiment, a lithographic apparatus includes an illumination optical system that may be configured to illuminate a pattern of a patterning device, a projection system that may be configured to project an image of the pattern on to a target portion of a substrate, and an inspection apparatus that may be configured to measure a property of the substrate includes an objective lens system. The objective lens system may comprise a first lens group that may be configured to correct field curvature aberrations and pupil aberrations of the objective lens system. The first lens group may comprise a bi-concave lens and a doublet lens.

In a further embodiment, an objective lens system includes first and second meniscus lenses positioned at a distance from each other along an optical axis of the objective lens system. The distance may be dependent on a focal length of the objective lens system. The objective lens system may further include third and fourth meniscus lenses in contact with each other, a bi-convex lens in contact with the fourth meniscus lens, a triplet lens, and an aperture stop between the triplet lens and the bi-convex lens.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention.

FIGS. 6 to 9 are schematic illustrations of a cross-sectional view of refractive objective lens systems, according to various embodiments of the invention.

Figure 1A:
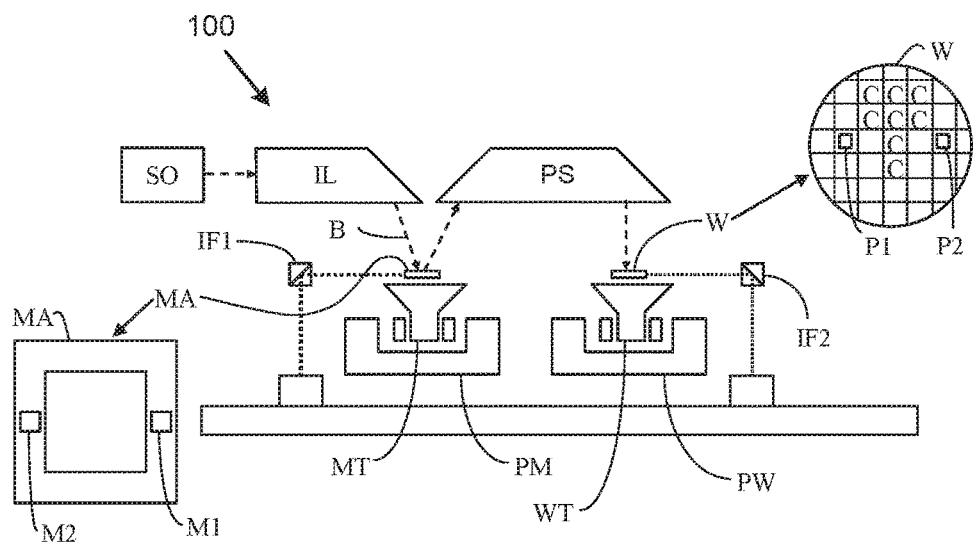
FIG. 1A is a schematic illustration of a reflective lithographic apparatus according to an embodiment of the invention.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number. Unless otherwise indicated, the drawings provided throughout the disclosure should not be interpreted as to-scale drawings.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment," "an embodiment," "an example embodiment," etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Before describing such embodiments in more detail, however, it is instructive to present an example environment in which embodiments of the present invention may be implemented.

Example Reflective and Transmissive Lithographic Systems

Figure 1B:
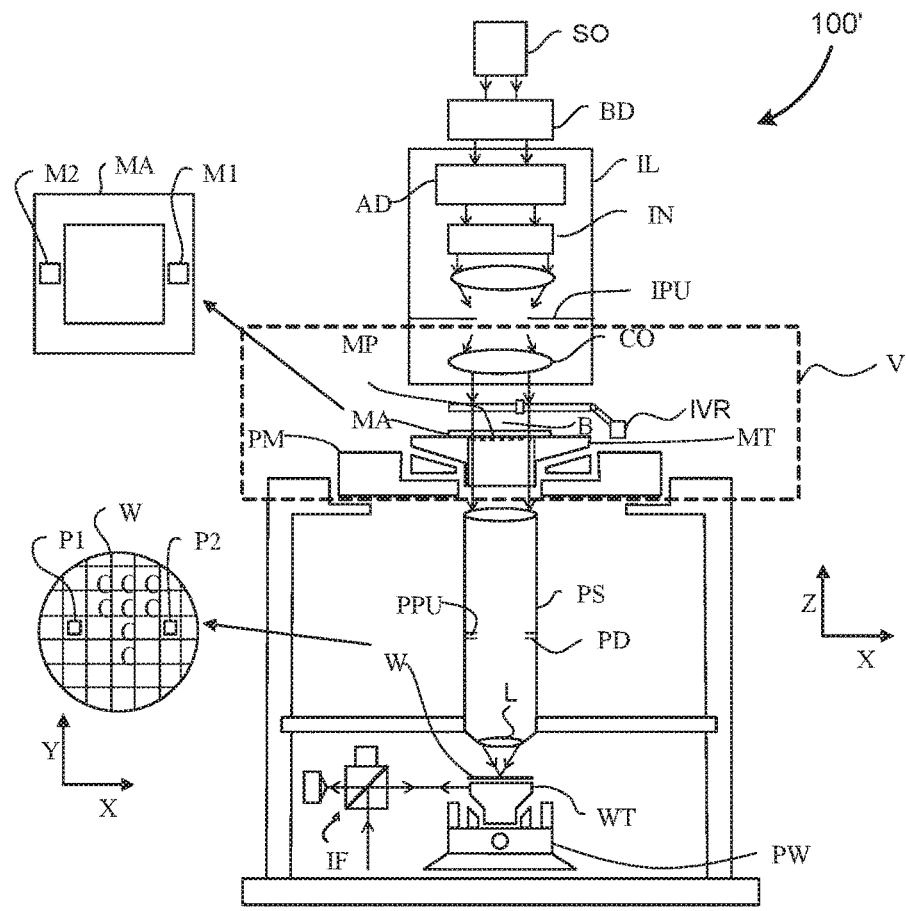
FIG. 1B is a schematic illustration of a transmissive lithographic apparatus according to an embodiment of the invention.

FIGS. 1A and 1B are schematic illustrations of a lithographic apparatus 100 and lithographic apparatus 100', respectively, in which embodiments of the present invention may be implemented. Lithographic apparatus 100 and lithographic apparatus 100' each include the following: an illumination system (illuminator) IL configured to condition a radiation beam B (for example, deep ultra violet or extreme ultra violet radiation); a support structure (for example, a mask table) MT configured to support a patterning device (for example, a mask, a reticle, or a dynamic patterning device) MA and connected to a first positioner PM configured to accurately position the patterning device MA; and, a substrate table (for example, a wafer table) WT configured to hold a substrate (for example, a resist coated wafer) W and connected to a second positioner PW configured to accurately position the substrate W. Lithographic apparatus 100 and 100' also have a projection system PS configured to project a pattern imparted to the radiation beam B by patterning device MA onto a target portion (for example, comprising one or more dies) C of the substrate W. In lithographic apparatus 100, the patterning device MA and the projection system PS are reflective. In lithographic apparatus 100', the patterning device MA and the projection system PS are transmissive.

The illumination system IL may include various types of optical components, such as refractive, reflective, catadioptric, magnetic, electromagnetic, electrostatic, or other types of optical components, or any combination thereof, for directing, shaping, or controlling the radiation beam B.

The support structure MT holds the patterning device MA in a manner that depends on the orientation of the patterning device MA with respect to a reference frame, the design of at least one of the lithographic apparatus 100 and 100', and other conditions, such as whether or not the patterning device MA is held in a vacuum environment. The support structure MT may use mechanical, vacuum, electrostatic, or other clamping techniques to hold the patterning device MA. The support structure MT can be a frame or a table, for example, which can be fixed or movable, as required. By using sensors, the support structure MT can ensure that the patterning device MA is at a desired position, for example, with respect to the projection system PS.

The term "patterning device" MA should be broadly interpreted as referring to any device that can be used to impart a radiation beam B with a pattern in its cross-section, such as to create a pattern in the target portion C of the substrate W. The pattern imparted to the radiation beam B can correspond to a particular functional layer in a device being created in the target portion C to form an integrated circuit.

The patterning device MA may be transmissive (as in lithographic apparatus 100' of FIG. 1B) or reflective (as in lithographic apparatus 100 of FIG. 1A). Examples of patterning devices MA include reticles, masks, programmable mirror arrays, and programmable LCD panels. Masks are well known in lithography, and include mask types such as binary, alternating phase shift, and attenuated phase shift, as well as various hybrid mask types. An example of a programmable mirror array employs a matrix arrangement of small mirrors, each of which can be individually tilted so as to reflect an incoming radiation beam in different directions. The tilted mirrors impart a pattern in the radiation beam B which is reflected by a matrix of small mirrors.

The term "projection system" PS can encompass any type of projection system, including refractive, reflective, catadioptric, magnetic, electromagnetic and electrostatic optical systems, or any combination thereof, as appropriate for the exposure radiation being used, or for other factors, such as the use of an immersion liquid on the substrate W or the use of a vacuum. A vacuum environment can be used for EUV or electron beam radiation since other gases can absorb too much radiation or electrons. A vacuum environment can therefore be provided to the whole beam path with the aid of a vacuum wall and vacuum pumps.

Lithographic apparatus 100 and/or lithographic apparatus 100' can be of a type having two (dual stage) or more substrate tables WT (and/or two or more mask tables). In such "multiple stage" machines, the additional substrate tables WT can be used in parallel, or preparatory steps can be carried out on one or more tables while one or more other substrate tables WT are being used for exposure. In some situations, the additional table may not be a substrate table WT.

Referring to FIGS. 1A and 1B, the illuminator IL receives a radiation beam from a radiation source SO. The source SO and the lithographic apparatus 100, 100' can be separate physical entities, for example, when the source SO is an excimer laser. In such cases, the source SO is not considered to form part of the lithographic apparatus 100 or 100', and the radiation beam B passes from the source SO to the illuminator IL with the aid of a beam delivery system BD (in FIG. 1B) including, for example, suitable directing mirrors and/or a beam expander. In other cases, the source SO can be an integral part of the lithographic apparatus 100, 100'—for example when the source SO is a mercury lamp. The source SO and the illuminator IL, together with the beam delivery system BD, if required, can be referred to as a radiation system.

The illuminator IL can include an adjuster AD (in FIG. 1B) for adjusting the angular intensity distribution of the radiation beam. Generally, at least the outer and/or inner radial extent (commonly referred to as "σ-outer" and "σ-inner," respectively) of the intensity distribution in a pupil plane of the illuminator can be adjusted. In addition, the illuminator IL can comprise various other components (in FIG. 1B), such as an integrator IN and a condenser CO. The illuminator IL can be used to condition the radiation beam B to have a desired uniformity and intensity distribution in its cross section.

Referring to FIG. 1A, the radiation beam B is incident on the patterning device (for example, mask) MA, which is held on the support structure (for example, mask table) MT, and is patterned by the patterning device MA. In lithographic apparatus 100, the radiation beam B is reflected from the patterning device (for example, mask) MA. After being reflected from the patterning device (for example, mask) MA, the radiation beam B passes through the projection system PS, which focuses the radiation beam B onto a target portion C of the substrate W. With the aid of the second positioner PW and position sensor IF2 (for example, an interferometric device, linear encoder, or capacitive sensor), the substrate table WT can be moved accurately (for example, so as to position different target portions C in the path of the radiation beam B). Similarly, the first positioner PM and another position sensor IF 1 can be used to accurately position the patterning device (for example, mask) MA with respect to the path of the radiation beam B. Patterning device (for example, mask) MA and substrate W can be aligned using mask alignment marks M1, M2 and substrate alignment marks P1, P2.

Referring to FIG. 1B, the radiation beam B is incident on the patterning device (for example, mask MA), which is held on the support structure (for example, mask table MT), and is patterned by the patterning device. Having traversed the mask MA, the radiation beam B passes through the projection system PS, which focuses the beam onto a target portion C of the substrate W. The projection system has a pupil PPU conjugate to an illumination system pupil IPU. Portions of radiation emanate from the intensity distribution at the illumination system pupil IPU and traverse a mask pattern without being affected by diffraction at a mask pattern and create an image of the intensity distribution at the illumination system pupil IPU.

With the aid of the second positioner PW and position sensor IF (for example, an interferometric device, linear encoder, or capacitive sensor), the substrate table WT can be moved accurately (for example, so as to position different target portions C in the path of the radiation beam B). Similarly, the first positioner PM and another position sensor (not shown in FIG. 1B) can be used to accurately position the mask MA with respect to the path of the radiation beam B (for example, after mechanical retrieval from a mask library or during a scan).

In general, movement of the mask table MT can be realized with the aid of a long-stroke module (coarse positioning) and a short-stroke module (fine positioning), which form part of the first positioner PM. Similarly, movement of the substrate table WT can be realized using a long-stroke module and a short-stroke module, which form part of the second positioner PW. In the case of a stepper (as opposed to a scanner), the mask table MT can be connected to a short-stroke actuator only or can be fixed. Mask MA and substrate W can be aligned using mask alignment marks M1, M2, and substrate alignment marks P1, P2. Although the substrate alignment marks (as illustrated) occupy dedicated target portions, they can be located in spaces between target portions (known as scribe-lane alignment marks). Similarly, in situations in which more than one die is provided on the mask MA, the mask alignment marks can be located between the dies.

Mask table MT and patterning device MA can be in a vacuum chamber, where an in-vacuum robot IVR can be used to move patterning devices such as a mask in and out of vacuum chamber. Alternatively, when mask table MT and patterning device MA are outside of the vacuum chamber, an out-of-vacuum robot can be used for various transportation operations, similar to the in-vacuum robot IVR. Both the in-vacuum and out-of-vacuum robots need to be calibrated for a smooth transfer of any payload (e.g., mask) to a fixed kinematic mount of a transfer station.

The lithographic apparatus 100 and 100' can be used in at least one of the following modes:

1. In step mode, the support structure (for example, mask table) MT and the substrate table WT are kept essentially stationary, while an entire pattern imparted to the radiation beam B is projected onto a target portion C at one time (i.e., a single static exposure). The substrate table WT is then shifted in the X and/or Y direction so that a different target portion C can be exposed.

2. In scan mode, the support structure (for example, mask table) MT and the substrate table WT are scanned synchronously while a pattern imparted to the radiation beam B is projected onto a target portion C (i.e., a single dynamic exposure). The velocity and direction of the substrate table WT relative to the support structure (for example, mask table) MT can be determined by the (de-)magnification and image reversal characteristics of the projection system PS.

3. In another mode, the support structure (for example, mask table) MT is kept substantially stationary holding a programmable patterning device, and the substrate table WT is moved or scanned while a pattern imparted to the radiation beam B is projected onto a target portion C. A pulsed radiation source SO can be employed and the programmable patterning device is updated as required after each movement of the substrate table WT or in between successive radiation pulses during a scan. This mode of operation can be readily applied to maskless lithography that utilizes a programmable patterning device, such as a programmable mirror array.

Combinations and/or variations on the described modes of use or entirely different modes of use can also be employed.

In a further embodiment, lithographic apparatus 100 includes an extreme ultraviolet (EUV) source, which is configured to generate a beam of EUV radiation for EUV lithography. In general, the EUV source is configured in a radiation system, and a corresponding illumination system is configured to condition the EUV radiation beam of the EUV source.

Figure 2:
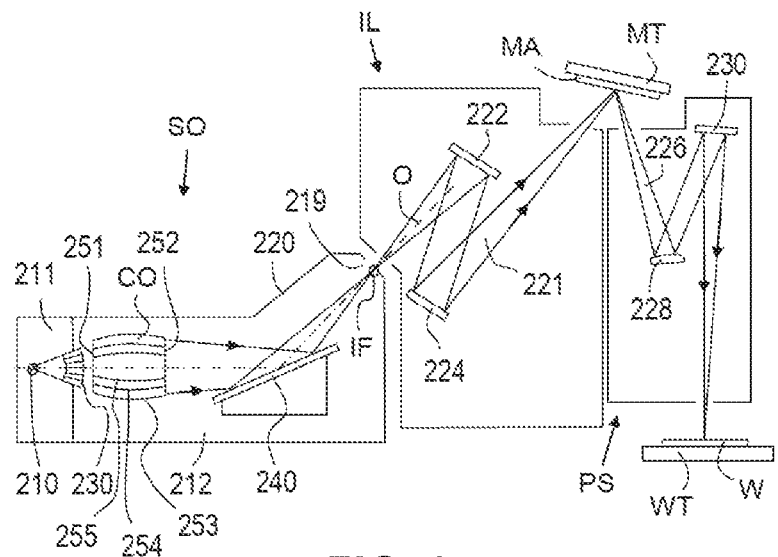
FIG. 2 is a more detailed schematic illustration of the reflective lithographic apparatus, according to an embodiment of the invention.

FIG. 2 shows the lithographic apparatus 100 in more detail, including the source collector apparatus SO, the illumination system IL, and the projection system PS. The source collector apparatus SO is constructed and arranged such that a vacuum environment can be maintained in an enclosing structure 220 of the source collector apparatus SO. An EUV radiation emitting plasma 210 may be formed by a discharge produced plasma source. EUV radiation may be produced by a gas or vapor, for example Xe gas, Li vapor or Sn vapor in which the very hot plasma 210 is created to emit radiation in the EUV range of the electromagnetic spectrum. The very hot plasma 210 is created by, for example, an electrical discharge causing an at least partially ionized plasma. Partial pressures of, for example, 10 Pa of Xe, Li, Sn vapor or any other suitable gas or vapor may be required for efficient generation of the radiation. In an embodiment, a plasma of excited tin (Sn) is provided to produce EUV radiation.

The radiation emitted by the hot plasma 210 is passed from a source chamber 211 into a collector chamber 212 via an optional gas barrier or contaminant trap 230 (in some cases also referred to as contaminant barrier or foil trap) which is positioned in or behind an opening in source chamber 211. The contaminant trap 230 may include a channel structure. Contamination trap 230 may also include a gas barrier or a combination of a gas barrier and a channel structure. The contaminant trap or contaminant barrier 230 further indicated herein at least includes a channel structure, as known in the art.

The collector chamber 212 may include a radiation collector CO which may be a so-called grazing incidence collector. Radiation collector CO has an upstream radiation collector side 251 and a downstream radiation collector side 252. Radiation that traverses collector CO can be reflected off a grating spectral filter 240 to be focused in a virtual source point IF. The virtual source point IF is commonly referred to as the intermediate focus, and the source collector apparatus is arranged such that the intermediate focus IF is located at or near an opening 219 in the enclosing structure 220. The virtual source point IF is an image of the radiation emitting plasma 210. Grating spectral filter 240 is used in particular for suppressing infra-red (IR) radiation.

Subsequently the radiation traverses the illumination system IL, which may include a facetted field mirror device 222 and a facetted pupil mirror device 224 arranged to provide a desired angular distribution of the radiation beam 221, at the patterning device MA, as well as a desired uniformity of radiation intensity at the patterning device MA. Upon reflection of the beam of radiation 221 at the patterning device MA, held by the support structure MT, a patterned beam 226 is formed and the patterned beam 226 is imaged by the projection system PS via reflective elements 228, 230 onto a substrate W held by the wafer stage or substrate table WT.

More elements than shown may generally be present in illumination optics unit IL and projection system PS. The grating spectral filter 240 may optionally be present, depending upon the type of lithographic apparatus. Further, there may be more mirrors present than those shown in the FIGs., for example there may be 1-6 additional reflective elements present in the projection system PS than shown in FIG. 2.

Collector optic CO, as illustrated in FIG. 2, is depicted as a nested collector with grazing incidence reflectors 253, 254 and 255, just as an example of a collector (or collector mirror). The grazing incidence reflectors 253, 254 and 255 are disposed axially symmetric around an optical axis O and a collector optic CO of this type is preferably used in combination with a discharge produced plasma source, often called a DPP source.

Example Lithographic Cell

Figure 3:
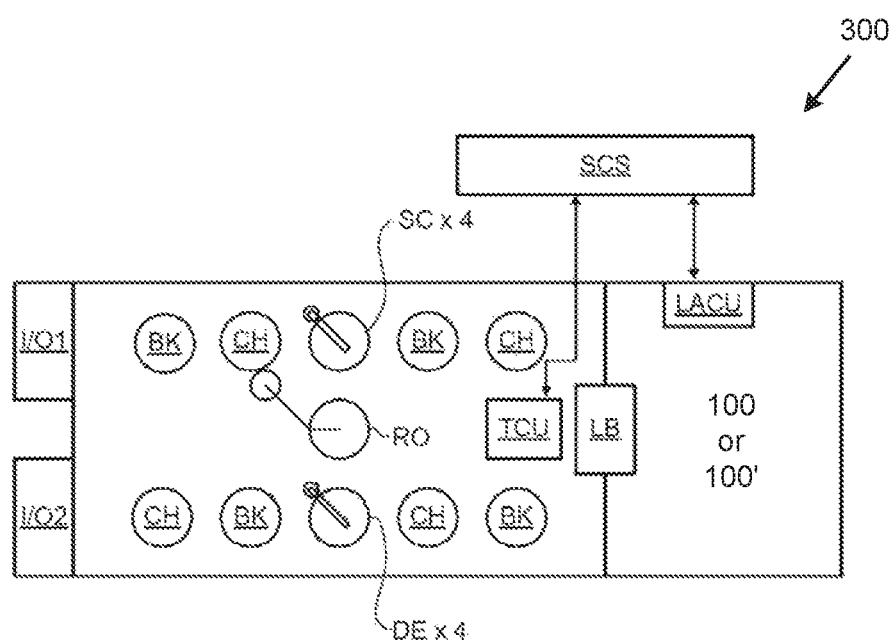
FIG. 3 is a schematic illustration of a lithographic cell, according to an embodiment of the invention.

FIG. 3 shows a lithographic cell 300, also sometimes referred to a lithocell or cluster. Lithographic apparatus 100 or 100' may form part of lithographic cell 300. Lithographic cell 300 may also include apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

Example Scatterometers

In order to ensure that the substrates that are exposed by a lithographic apparatus, such as lithographic apparatus 100 and/or 100' are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded, thereby avoiding performing exposures on substrates that are known to be faulty. In a case where only some target portions of a substrate are faulty, further exposures can be performed only on those target portions which are good.

An inspection apparatus may be used to determine the properties of the substrates, and in particular, how the properties of different substrates or different layers of the same substrate vary from layer to layer. The inspection apparatus may be integrated into a lithographic apparatus, such as lithographic apparatus 100 and/or 100' or lithocell 300 or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 4:
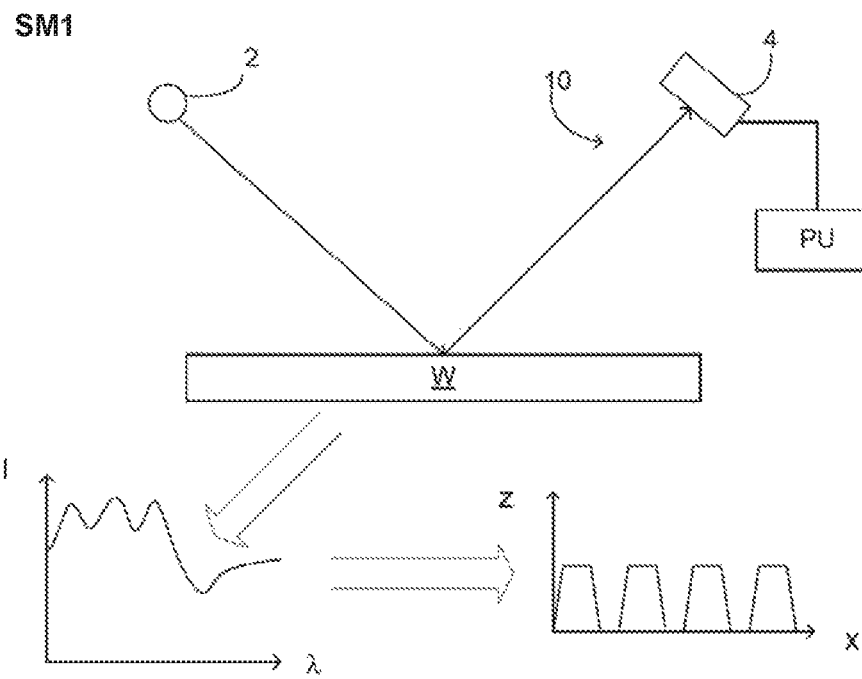
FIGS. 4 and 5 are schematic illustrations of scatterometers, according to various embodiments of the invention.

FIG. 4 depicts a scatterometer SM1 which may be used in the present invention. Scatterometer SM1 may be integrated into a lithographic apparatus, such as lithographic apparatus 100 and/or 100' or lithocell 300 or may be a stand-alone device. It comprises a broadband (white light) radiation projector 2 which projects radiation onto a substrate W. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU, e.g., by Rigorous Coupled Wave Analysis and non-linear regression or by comparison with a library of simulated spectra as shown at the bottom of FIG. 4. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 5:
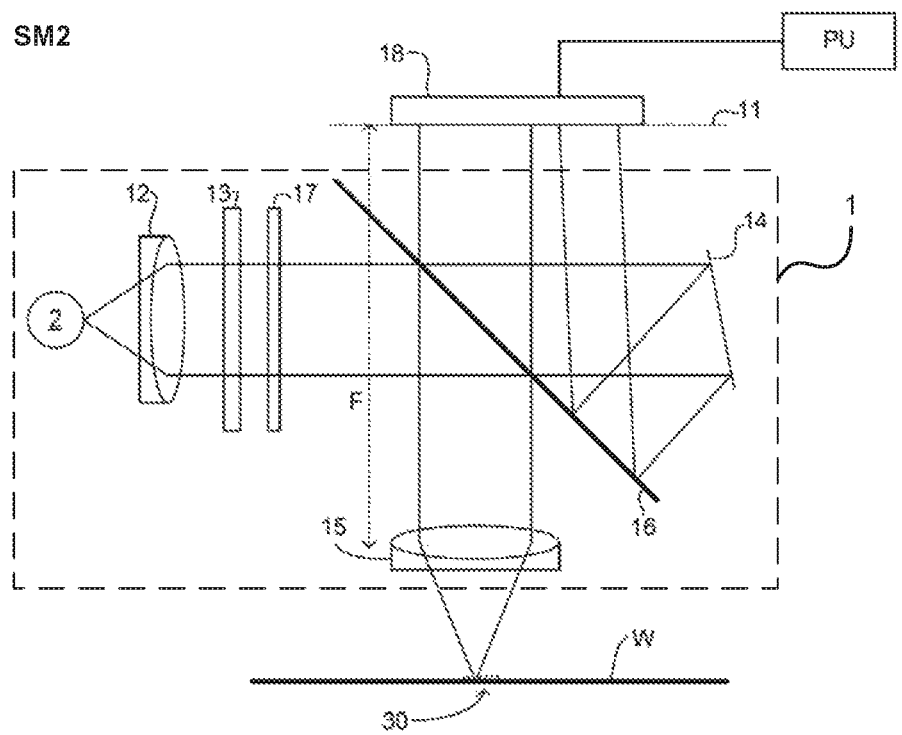

Another scatterometer SM2 that may be used with the present invention is shown in FIG. 5. Scatterometer SM2 may be integrated into a lithographic apparatus, such as lithographic apparatus 100 and/or 100' or lithocell 300 or may be a stand-alone device. Scatterometer SM2 may include an optical system 1 having a radiation source 2, a lens system 12, a filter 13 (e.g., interference filter), a reflecting device 14 (e.g., reference mirror), a lens system 15 (e.g., a microscopic objective lens system, also referred herein as objective lens system), a partially reflected surface 16 (e.g., a beam splitter), and a polarizer 17. Scatterometer SM2 may further include a detector 18 and a processing unit PU.

Objective lens system 15 may have a high numerical aperture (NA), e.g., at least 0.9 or at least 0.95. Immersion scatterometers may even have objective lenses with numerical apertures over 1.

In one exemplary operation, the radiation emitted by radiation source 2 is collimated using lens system 12 and transmitted through interference filter 13 and polarizer 17, is reflected by partially reflected surface 16 and is focused onto substrate W via microscope objective lens system 15. The reflected radiation then transmits through partially reflecting surface 16 into a detector 18 in order to have the scatter spectrum detected. The detector may be located in the back-projected pupil plane 11, which is at the focal length of the objective lens system 15, however the pupil plane may instead be re-imaged with auxiliary optics (not shown) onto the detector. The pupil plane is the plane in which the radial position of radiation defines the angle of incidence and the angular position defines azimuth angle of the radiation. In one example, the detector is a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam may be used, for example, to measure the intensity of the incident radiation. To do this, when the radiation beam is incident on beam splitter 16 part of it is transmitted through the beam splitter as a reference beam towards reference mirror 14. The reference beam is then projected onto a different part of the same detector 18 or alternatively on to a different detector (not shown).

Interference filter 13 may include a set of interference filters, which may be available to select a wavelength of interest in the range of, say, 405-790 nm or even lower, such as 200-300 nm. The interference filter may be tunable rather than comprising a set of different filters. A grating could be used instead of interference filters.

Detector 18 may measure the intensity of scattered light at a single wavelength (or narrow wavelength range), the intensity separately at multiple wavelengths or integrated over a wavelength range. Furthermore, detector 18 may separately measure the intensity of transverse magnetic- and transverse electric-polarized light and/or the phase difference between the transverse magnetic- and transverse electric-polarized light.

Using a broadband light source (i.e., one with a wide range of light frequencies or wavelengths—and therefore of colors) for a radiation source 2 may give a large etendue, allowing the mixing of multiple wavelengths. The plurality of wavelengths in the broadband preferably each may have a bandwidth of $\Delta\lambda$ and a spacing of at least $2\Delta\lambda$ (i.e., twice the bandwidth). Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP1,628,164A, which is incorporated by reference herein in its entirety.

The target 30 on substrate W may be a 1-D grating, which is printed such that after development, the bars are formed of solid resist lines. The target 30 may be a 2-D grating, which is printed such that after development, the grating is formed of solid resist pillars or vias in the resist. The bars, pillars or vias may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the 1-D grating, such as line widths and shapes, or parameters of the 2-D grating, such as pillar or via widths or lengths or shapes, may be input to the reconstruction process, performed by processing unit PU, from knowledge of the printing step and/or other scatterometry processes.

As described above, the target can be on the surface of the substrate. This target will often take the shape of a series of lines in a grating or substantially rectangular structures in a 2-D array. The purpose of rigorous optical diffraction theories in metrology is effectively the calculation of a diffraction spectrum that is reflected from the target. In other words, target shape information is obtained for CD (critical dimension) uniformity and overlay metrology. Overlay metrology is a measuring system in which the overlay of two targets is measured in order to determine whether two layers on a substrate are aligned or not. CD uniformity is simply a measurement of the uniformity of the grating on the spectrum to determine how the exposure system of the lithographic apparatus is functioning. Specifically, CD, or critical dimension, is the width of the object that is "written" on the substrate and is the limit at which a lithographic apparatus is physically able to write on a substrate.

Objective Lens System according to a First Embodiment

Figure 6:
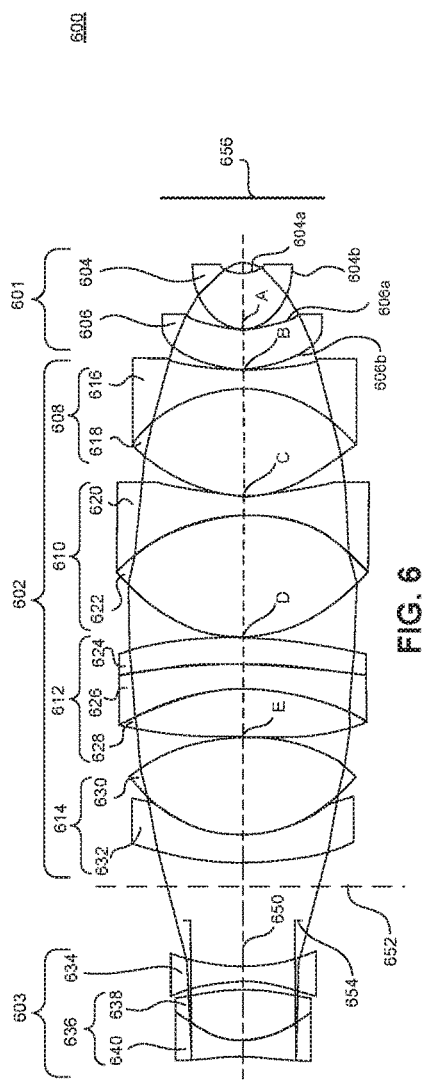

FIG. 6 illustrates a schematic of a cross-sectional view of a refractive objective lens system 600 that can be implemented as a part of scatterometers SM1 and/or SM2 (shown in FIGS. 4 and 5), according to an embodiment. In an example of this embodiment, objective lens system 600 may be used for directing and/or focusing a radiation beam emitted from an illumination system (not shown) onto an object of inspection (e.g., patterning device MA, target 30 on substrate W, target portion C), and for collecting and/or imaging the scattered or reflected light from the object of inspection.

Objective lens system 600 may be configured to have a high NA (e.g., NA equal to about 0.95, NA greater than about 0.95, NA equal to about 1) without central obscuration, a large working distance (e.g., greater than about 0.35, greater than about 0.5) and low optical aberrations (e.g., low chromatic aberrations, low field curvature aberrations, low pupil aberrations, low apochromatic aberrations) compared to current objective lens system. Additionally, objective lens system 600 may be configured to have a focal length ranging from about 3.5 vmm to about 3.6 mm. Further, objective lens system 600 may be configured to operate over a wider spectral band of wavelengths (e.g., between 450-700 nm wavelengths, below 450 nm wavelength, above 700 nm wavelength, between 410-450 nm wavelengths, between 700-900 nm wavelengths, at deep ultra violet (DUV) wavelengths, at infrared (IR) wavelengths) compared to current objective lens systems without compromising optical performance.

According to an example of this embodiment, objective lens system 600 may comprise a front lens group 601, a middle lens group 602, and a back lens group 603. Front lens group 601, middle lens group 602, and back lens group 603 may be optically coupled to each other and may be arranged along optical axis 650 of objective lens system 600.

Front lens group 601 may be configured to decrease NA from an object space 656 to the entrance of middle lens group 602, according to an example of this embodiment. For example, front lens group 601 may decrease NA from about 0.95 in the object space to about 0.25-0.4 at the entrance of middle lens group 602. According to another example, front lens group 601 may be configured to simultaneously correct or reduce coma aberrations and chromatic aberrations (axial color aberrations) of objective lens system 600. Such configurations of front lens group 601 may be dependent on composition and arrangement of one or more lenses in front lens group 601.

In an example of this embodiment, front lens group 601 may comprise a first positive meniscus lens 604 and a second positive meniscus lens 606 that are optically coupled to each other (shown in FIG. 6). First positive meniscus lens 604 may have a spherical concave surface 604a and a spherical convex surface 604b, and second positive meniscus lens 606 may have a spherical concave surface 606a and a spherical convex surface 606b. Convex surface 604b may have a radius of curvature that is smaller than a radius of curvature of convex surface 606b. Convex surface 604b may be in substantial contact with concave surface 606a at least at a point A along optical axis 650, according to an example. In another example, an air gap ranging from about 2% to about 8% of the focal length of objective lens system 600 may be present between convex surface 604b and concave surface 606a along optical axis 650.

First positive meniscus lens 604 may comprise, e.g., a heavy crown glass, a heavy flint glass, a lanthanum flint glass, a lanthanum dense flint glass, or a combination thereof having a refractive index greater than about 1.75, according to various examples of this embodiment. In other examples of this embodiment, first positive meniscus lens 604 may comprise an optical material having an Abbe number that ranges from about 45 to about 50, that is greater than 50, or that is greater than 70.

One lens parameter is its Abbe number, which is a measure of the material's dispersion (variation of refractive index with wavelength) in relation to the refractive index. High Abbe numbers indicate low dispersion (low chromatic aberration), and vice versa. Second positive meniscus lens 606 may comprise a heavy flint glass having an Abbe number and a refractive index smaller than the Abbe number and refractive index of first positive meniscus lens 604. For example, second positive meniscus lens 606 may have an Abbe number less than about 30 and a refractive index that ranges from about 1.5 to about 1.6. The large difference (e.g., greater than about 15) in the Abbe numbers of first positive meniscus lens 604 and second positive meniscus lens 606 may allow the correction or reduction of coma and chromatic aberrations by front lens group 601. For example, if first positive meniscus lens 604 comprises an optical material having an Abbe number of about 45 and second positive meniscus lens 606 comprises an optical material having an Abbe number of about 29, the difference in Abbe numbers is equal to about 16.

In an embodiment, middle lens group 602 may be configured to correct or reduce apochromatic aberrations of objective lens system 600. Such configuration of middle lens group 602 may be dependent on composition and arrangement of one or more lenses in middle lens group 602. Middle lens group 602 may comprise a first doublet lens 608, a second doublet lens 610, a triplet lens 612, and a third doublet 614, as shown in FIG. 6, according to an example of this embodiment.

First doublet lens 608 may comprise a bi-concave lens 616 and a bi-convex lens 618 and may be positioned in a manner that first bi-concave lens 616 is in substantial contact with second positive meniscus lens 606 at least at a point B along optical axis 650, as illustrated in FIG. 6. Also, as illustrated in FIG. 6, bi-concave lens 616 may have a thickness along optical axis 650 that is smaller than a thickness of bi-convex lens 618 along optical axis 650. Bi-concave lens 616 and bi-convex lens 618 may be coupled together and may have spherical surfaces. The coupling of bi-concave lens 616 and bi-convex lens 618 may be achieved by cementing these lenses to each other, according to an example. The lenses may be cemented by an adhesive (e.g., optically transparent epoxy) with mechanical strength to hold these lenses together. In another example, bi-concave lens 616 and bi-convex lens 618 may be coupled by holding these lenses pressed against each other with external mounting fixtures because the optical design may require an infinitesimal air gap between these lenses or because the difference in thermal expansion coefficients of these lenses does not allow cementing. The external mounting fixtures may hold these lenses together in a manner such that a partial or an entire surface of bi-concave lens 616 is in substantial contact with a partial or an entire surface of bi-convex lens 618. Bi-concave lens 616 and bi-convex lens 618 may comprise materials such as, but not limited to, crown glass or flint glass. Both bi-concave lens 616 and bi-convex lens 618 may comprise the same material or different material with respect to each other.

Second doublet lens 610 may comprise a bi-concave lens 620 and a bi-convex lens 622 and may be positioned in a manner that bi-concave lens 620 is in substantial contact with bi-convex surface 618 at least at a point C along optical axis 650, as illustrated in FIG. 6. Also, as illustrated in FIG. 6, bi-concave lens 620 may have a thickness along optical axis 650 that is smaller than a thickness of bi-convex lens 622 along optical axis 650. Bi-concave lens 620 and bi-convex lens 622 may have spherical surfaces and may be coupled together by cementing or by holding together, as described above with reference to bi-concave lens 616 and bi-convex lens 618. Bi-concave lens 620 and bi-convex lens 622 may comprise materials such as, but not limited to, crown glass material or flint glass material. Both bi-concave lens 620 and bi-convex lens 622 may comprise the same material or different material with respect to each other.

Triplet lens 612 may comprise a positive meniscus lens 624, a negative meniscus lens 626, and a bi-convex lens 628 and may be positioned in a manner that positive meniscus lens 624 is in substantial contact with bi-convex surface 622 at least at a point D along optical axis 650, as illustrated in FIG. 6. Positive meniscus lens 624, negative meniscus lens 626, and bi-convex lens 628 may have spherical surfaces and may be coupled together by cementing or by holding together, as described above with reference to bi-concave lens 616 and bi-convex lens 618.

In one example, bi-convex lens 628 may have a thickness along optical axis 650 that is greater than each thickness of positive meniscus lens 624 and negative meniscus lens 626 along optical axis 650. In another example, bi-convex lens 628 may have a thickness along optical axis 650 that is greater than combined thickness of positive meniscus lens 624 and negative meniscus lens 626 along optical axis 650. In a further example, thickness of positive meniscus lens 624 and thickness of negative meniscus lens 626 along optical axis 650 is equal or different with respect to each other.

According to an example, positive meniscus lens 624 may comprise calcium fluoride ($CaF_2$), negative meniscus lens 626 may comprise a heavy crown glass, a heavy flint glass, a lanthanum flint glass, or a lanthanum dense flint glass, and bi-convex lens 628 may comprise a heavy flint glass having a refractive index that is greater than about 1.75. These combinations of glass materials in triplet lens 612 may allow middle lens group 602 to correct or reduce apochromatic aberrations of objective lens system 600.

As further illustrated in FIG. 6, third doublet lens 614 may comprise a bi-convex lens 630 and a positive meniscus lens 632 and may be positioned in a manner that bi-convex lens 630 is in substantial contact with bi-convex lens 628 at least at a point E along optical axis 650. Also, as illustrated in FIG. 6, bi-convex lens 630 may have a thickness along optical axis 650 that is greater than a thickness of positive meniscus lens 632 along optical axis 650. Bi-convex lens 630 and positive meniscus lens 632 may have spherical surfaces and may be coupled together by cementing or by holding together, as described above with reference to bi-concave lens 616 and bi-convex lens 618.

According to an embodiment, back lens group 603 may be configured to correct or reduce field curvature (also sometimes referred as Petzval curvature in the art) aberrations and pupil aberrations of objective lens system 600. Such configuration of back lens group 603 may be dependent on composition and arrangement of one or more lenses in back lens group 603. Back lens group 603 may comprise a bi-convex lens 634 and a doublet lens 636 that are placed adjacent to each other, but are not in contact with each other, as shown in FIG. 6, according to an example of this embodiment. Doublet lens 636 may comprise a bi-convex lens 638 and a bi-concave lens 640. Bi-convex lens 638 may have a thickness along optical axis 650 that is greater than each thickness of bi-concave lenses 634 and 640 along optical axis 650. Bi-convex lens 638 and bi-concave lens 640 may have spherical surfaces and may be coupled together by cementing or by holding together, as described above with reference to bi-concave lens 616 and bi-convex lens 618.

Further, as illustrated in FIG. 6, objective lens system 600 may comprise an aperture stop 652 and an entrance pupil 654 that may be located along optical axis 650 and between middle lens group 602 and back group lens 603, according to an example of this embodiment. Location of entrance pupil 626 between middle lens group 602 and back lens group 618 may allow a diameter of aperture stop 624 to be adjusted.

Objective Lens System according to a Second Embodiment

Figure 7:
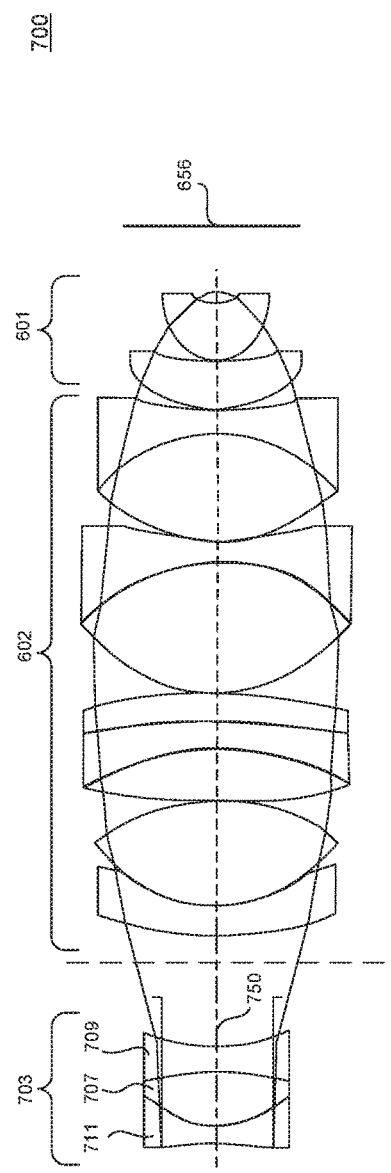

FIG. 7 illustrates a schematic of a cross-sectional view of a refractive objective lens system 700 that can be implemented as a part of scatterometers SM1 and/or SM2 (shown in FIGS. 4 and 5), according to an embodiment. Objective lens system 700 shares many similar features and configurations with objective lens system 600. Therefore, only differences between objective lens systems 600 and 700 are to be discussed below.

According to an example of this embodiment, objective lens system 700 may comprise a front lens group 601, a middle lens group 602, and a back lens group 703. Front lens group 601, middle lens group 602, and back lens group 703 may be optically coupled to each other and may be arranged along optical axis 750 of objective lens system 700.

Back lens group 703 may comprise a bi-convex lens 707 interposed between two bi-concave lenses 709 and 711, according to an example of this embodiment. Bi-convex lens 638 and bi-concave lenses 709 and 711 may have spherical surfaces and may be coupled together to form a triplet lens by cementing or by holding together, as described above with reference to bi-concave lens 616 and bi-convex lens 618 (shown in FIG. 6). Bi-convex lens 707 may have a thickness along optical axis 750 that is greater than each thickness of bi-concave lenses 709 and 711 along optical axis 750. Such combination of lenses may allow back group lens 703 to correct or reduce field curvature aberrations and pupil aberrations of objective lens system 700.

Objective Lens System according to a Third Embodiment

FIG. 8 illustrates a schematic of a cross-sectional view of a refractive objective lens system 800 that can be implemented as a part of scatterometers SM1 and/or SM2 (shown in FIGS. 4 and 5), according to an embodiment. Objective lens system 800 shares many similar features and configurations with objective lens systems 600 and 700. Therefore, only differences between objective lens systems 600, 700, and 800 are to be discussed below.

According to an example of this embodiment, objective lens system 800 may comprise a front lens group 801, a middle lens group 602, and a back lens group 703. Front lens group 801, middle lens group 602, and back lens group 703 may be optically coupled to each other and may be arranged along optical axis 850 of objective lens system 700.

Front lens group 801 is similar to front lens group 601 (shown in FIGS. 6-7), except that front lens group 801 includes an aspherical meniscus lens 805 instead of the positive spherical meniscus lens 606 of front lens group 601. Aspherical meniscus lens 805 may have an aspherical concave surface 805a and a spherical convex surface 805b. Aspherical concave surface 805a may be in substantial contact with spherical convex surface 803a at least at a point F along optical axis 850, according to an example. In another example, an air gap ranging from about 2% to about 8% of the focal length of objective lens system 800 may be present between aspherical concave surface 805a and spherical convex surface 803a along optical axis 850. Presence of aspherical concave surface 805a in front lens group 801 may offer optimal aberration correction and as a result higher resolution compared to front lens group 601 as aspherical surfaces inherently produce less optical aberrations (e.g., spherical aberrations) than spherical surfaces. In an example of this embodiment, aspherical meniscus lens 805 may comprise a heavy flint glass having an Abbe number and a refractive index similar to the Abbe number and refractive index of second positive meniscus lens 606 of front lens group 601.

Objective Lens System according to a Fourth Embodiment

FIG. 9 illustrates a schematic of a cross-sectional view of a refractive objective lens system 900 that can be implemented as a part of scatterometers SM1 and/or SM2 (shown in FIGS. 4 and 5), according to an embodiment. Objective lens system 900 shares many similar features and configurations with objective lens systems 600, 700, and 800. Therefore, only differences between objective lens systems 600, 700, and 800 are to be discussed below.

According to an example of this embodiment, objective lens system 900 may comprise a front lens group 601, a middle lens group 902, and a back lens group 703. Front lens group 601, middle lens group 902, and back lens group 703 may be optically coupled to each other and may be arranged along optical axis 950 of objective lens system 900.

Middle lens group 902 is similar to middle lens group 602 (shown in FIGS. 6-8), except for the differences described herein. In an example, middle lens group 902 includes a concave lens 905 and a bi-convex lens 907 forming a doublet lens 909 instead of the positive meniscus lens 632 and the bi-convex lens 630 forming the doublet lens 614 of middle lens group 602. In another example, middle group lens 902 includes a triplet lens 911 having meniscus lenses 913 and 915 and a bi-convex lens 917. Radii of curvature of spherical surfaces of meniscus lenses 913 and 915 are smaller than radii of curvature of the spherical surfaces of meniscus lenses 624 and 626 of middle lens group 602. These differences in middle lens group 902 from middle lens group 602 may allow objective lens system 900 to have a focal length smaller than the focal length of objective lens system 600, 700, and/or 800 for the same high NA as the objective lens systems 600, 700, and 800. For example, objective lens system 900 may have a focal length of 2 mm for a NA of 0.95.

It should be noted that even though objective lens system 900 is shown to include a front lens group similar to front lens group 601 of objective lens 600 and a back lens group similar to back lens group 703 of objective lens 700, objective lens system 900 may include front lens group that is similar to front lens group 801 of objective lens system 800 and/or a back lens group that is similar to back lens group 603 of objective lens system 600, according to various examples of this embodiment.

Although specific reference may be made in this text to the use an objective lens system in inspection system, it should be understood that the objective lens system described herein may have other applications that require a combination of high NA, large field of view (FOV), and/or wide spectral band.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

It is to be understood that the phraseology or terminology herein is for the purpose of description and not of limitation, such that the terminology or phraseology of the present specification is to be interpreted by those skilled in relevant art(s) in light of the teachings herein.

In the embodiments described herein, the terms "lens" and "lens element," where the context allows, can refer to any one or combination of various types of optical components, including refractive, reflective, magnetic, electromagnetic, and electrostatic optical components.

Further, the terms "radiation" and "beam" used herein encompass all types of electromagnetic radiation, including ultraviolet (UV) radiation (for example, having a wavelength $\lambda$ of 365, 248, 193, 157 or 126 nm), extreme ultraviolet (EUV or soft X-ray) radiation (for example, having a wavelength in the range of 5-20 nm such as, for example, 13.5 nm), or hard X-ray working at less than 5 nm, as well as particle beams, such as ion beams or electron beams. Generally, radiation having wavelengths between about 780-3000 nm (or larger) is considered IR radiation. UV refers to radiation with wavelengths of approximately 100-400 nm. Within lithography, the term "UV" also applies to the wavelengths that can be produced by a mercury discharge lamp: G-line 436 nm; H-line 405 nm; and/or, I-line 365 nm. Vacuum UV, or VUV (i.e., UV absorbed by gas), refers to radiation having a wavelength of approximately 100-200 nm. Deep UV (DUV) generally refers to radiation having wavelengths ranging from 126 nm to 428 nm, and in an embodiment, an excimer laser can generate DUV radiation used within a lithographic apparatus. It should be appreciated that radiation having a wavelength in the range of, for example, 5-20 nm relates to radiation with a certain wavelength band, of which at least part is in the range of 5-20 nm.

The term "substrate" as used herein describes a material onto which subsequent material layers are added. In embodiments, the substrate itself may be patterned and materials added on top of it may also be patterned, or may remain without patterning.

The term "in substantial contact" as used herein generally describes elements or structures that are in physical contact with each other with only a slight separation from each other which typically results from misalignment tolerances. It should be understood that relative spatial descriptions between one or more particular features, structures, or characteristics (e.g., "vertically aligned," "substantial contact," etc.) used herein are for purposes of illustration only, and that practical implementations of the structures described herein may include misalignment tolerances without departing from the spirit and scope of the present disclosure.

The term "optically coupled" as used herein generally refers to one coupled element being configured to impart light to another coupled element directly or indirectly.

The term "optical material" as used herein generally refers to a material that allows light or optical energy to propagate therein or therethrough.

While specific embodiments of the invention have been described above, it will be appreciated that the invention may be practiced otherwise than as described. The description is not intended to limit the invention.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein.

The breadth and scope of the present invention should not be limited by any of the above-described exemplary embodiments, but should be defined only in accordance with the following claims and their equivalents.

The invention claimed is:

1. An inspection system configured to measure a property of a substrate, the inspection system comprising:
   a radiation source configured to produce a radiation beam;
   an optical system configured to focus the radiation beam on to a surface of the substrate, the optical system comprising:
      a first lens group comprising:
         a first positive meniscus lens, and
         a second positive meniscus lens positioned at a distance from the first positive meniscus lens along an optical axis of the optical system, the distance being dependent on a focal length of the optical system, a second lens group comprising:
- a third positive meniscus lens,
- a negative meniscus lens cemented to the third positive meniscus lens, and
- a bi-convex lens cemented to the negative meniscus lens, and a third lens group comprising:
- a bi-concave lens, and
- a doublet lens; and a detector configured to detect the radiation beam reflected from the surface of the substrate.

2. The inspection system of claim 1, wherein the second positive meniscus lens comprises an aspherical concave surface.

3. The inspection system of claim 1, wherein:
the third positive meniscus lens comprises calcium fluoride;
the negative meniscus lens comprises a heavy crown glass, a heavy flint glass, a lanthanum flint glass, or a lanthanum dense flint glass; and
the bi-convex lens comprises a heavy flint glass having a refractive index that is greater than about 1.75.

4. The inspection system of claim 1, wherein the bi-concave lens and the doublet are adjacent to and separated from each other.

5. The inspection system of claim 1, wherein the bi-concave lens and the doublet are cemented to each other.

6. The inspection system of claim 1, wherein the third lens group is configured to correct field curvature aberrations and pupil aberrations of the optical system.

* * * * *